United States Patent
Luckemeyer et al.

(10) Patent No.: US 11,185,624 B2
(45) Date of Patent: Nov. 30, 2021

(54) NEGATIVE-PRESSURE THERAPY WITH DISPOSABLE INSTILLATION PUMP CHAMBER

(71) Applicant: KCI Licensing, Inc., San Antonio, TX (US)

(72) Inventors: James A. Luckemeyer, San Antonio, TX (US); Christopher Brian Locke, Bournemouth (GB); Benjamin Andrew Pratt, Poole (GB)

(73) Assignee: KCI Licensing, Inc., San Antonio, TX (US)

( * ) Notice: Subject to any disclaimer, the term of this patent is extended or adjusted under 35 U.S.C. 154(b) by 347 days.

(21) Appl. No.: 16/302,585

(22) PCT Filed: May 16, 2017

(86) PCT No.: PCT/US2017/032917
§ 371 (c)(1),
(2) Date: Nov. 16, 2018

(87) PCT Pub. No.: WO2017/209945
PCT Pub. Date: Dec. 7, 2017

(65) Prior Publication Data
US 2019/0290813 A1    Sep. 26, 2019

Related U.S. Application Data

(60) Provisional application No. 62/345,368, filed on Jun. 3, 2016.

(51) Int. Cl.
*A61M 1/00* (2006.01)
*A61M 3/02* (2006.01)

(52) U.S. Cl.
CPC ............ *A61M 1/90* (2021.05); *A61M 1/0062* (2013.01); *A61M 1/85* (2021.05); *A61M 3/0254* (2013.01); *A61M 2205/7518* (2013.01)

(58) Field of Classification Search
CPC .............. A61M 1/0088; A61M 1/0058; A61M 1/0062; A61M 1/0084; A61M 3/0254;
(Continued)

(56) References Cited

U.S. PATENT DOCUMENTS

| 1,355,846 A | 10/1920 | Rannells |
| 2,547,758 A | 4/1951 | Keeling |

(Continued)

FOREIGN PATENT DOCUMENTS

| AU | 550575 B2 | 3/1986 |
| AU | 745271 B2 | 3/2002 |

(Continued)

OTHER PUBLICATIONS

International Search Report and Written Opinion for Corresponding Application No. PCT/US2017/032917, dated Jul. 26, 2017.
(Continued)

*Primary Examiner* — Ariana Zimbouski

(57) ABSTRACT

Systems, apparatuses, and methods for instilling fluid to a tissue site in a negative-pressure therapy environment are described. Illustrative embodiments may include a pneumatically-actuated instillation pump that can draw a solution from a solution source during a negative-pressure interval, and instill the solution to a dressing during a venting interval. A pneumatic actuator may be mechanically coupled to a disposable distribution system that can provide a fluid path between the solution source and a distribution component. A bacterial filter may be disposed in the fluid path between the actuator and the distribution component to prevent contamination of the actuator during operation. The distribution system may be separated from the actuator and disposed of after operation, and the actuator may be re-used.

10 Claims, 6 Drawing Sheets

(58) Field of Classification Search
CPC ......... A61M 2205/7518; A61M 5/1424; A61F 13/00068

See application file for complete search history.

(56) References Cited

U.S. PATENT DOCUMENTS

| | | | |
|---|---|---|---|
| 2,632,443 | A | 3/1953 | Lesher |
| 2,682,873 | A | 7/1954 | Evans et al. |
| 2,910,763 | A | 11/1959 | Lauterbach |
| 2,969,057 | A | 1/1961 | Simmons |
| 3,066,672 | A | 12/1962 | Crosby, Jr. et al. |
| 3,367,332 | A | 2/1968 | Groves |
| 3,520,300 | A | 7/1970 | Flower, Jr. |
| 3,568,675 | A | 3/1971 | Harvey |
| 3,648,692 | A | 3/1972 | Wheeler |
| 3,682,180 | A | 8/1972 | McFarlane |
| 3,826,254 | A | 7/1974 | Mellor |
| 4,080,970 | A | 3/1978 | Miller |
| 4,096,853 | A | 6/1978 | Weigand |
| 4,139,004 | A | 2/1979 | Gonzalez, Jr. |
| 4,165,748 | A | 8/1979 | Johnson |
| 4,184,510 | A | 1/1980 | Murry et al. |
| 4,233,969 | A | 11/1980 | Lock et al. |
| 4,245,630 | A | 1/1981 | Lloyd et al. |
| 4,256,109 | A | 3/1981 | Nichols |
| 4,258,711 | A * | 3/1981 | Tucker .............. A61M 5/14276 604/502 |
| 4,261,363 | A | 4/1981 | Russo |
| 4,275,721 | A | 6/1981 | Olson |
| 4,284,079 | A | 8/1981 | Adair |
| 4,297,995 | A | 11/1981 | Golub |
| 4,333,468 | A | 6/1982 | Geist |
| 4,373,519 | A | 2/1983 | Errede et al. |
| 4,382,441 | A | 5/1983 | Svedman |
| 4,392,853 | A | 7/1983 | Muto |
| 4,392,858 | A | 7/1983 | George et al. |
| 4,419,097 | A | 12/1983 | Rowland |
| 4,465,485 | A | 8/1984 | Kashmer et al. |
| 4,475,909 | A | 10/1984 | Eisenberg |
| 4,480,638 | A | 11/1984 | Schmid |
| 4,525,166 | A | 6/1985 | Leclerc |
| 4,525,374 | A | 6/1985 | Vaillancourt |
| 4,540,412 | A | 9/1985 | Van Overloop |
| 4,543,100 | A | 9/1985 | Brodsky |
| 4,548,202 | A | 10/1985 | Duncan |
| 4,551,139 | A | 11/1985 | Plaas et al. |
| 4,569,348 | A | 2/1986 | Hasslinger |
| 4,605,399 | A | 8/1986 | Weston et al. |
| 4,608,041 | A | 8/1986 | Nielsen |
| 4,640,688 | A | 2/1987 | Hauser |
| 4,655,754 | A | 4/1987 | Richmond et al. |
| 4,664,662 | A | 5/1987 | Webster |
| 4,699,615 | A * | 10/1987 | Fischell .............. A61M 5/1424 128/DIG. 12 |
| 4,710,165 | A | 12/1987 | McNeil et al. |
| 4,733,659 | A | 3/1988 | Edenbaum et al. |
| 4,743,232 | A | 5/1988 | Kruger |
| 4,758,220 | A | 7/1988 | Sundblom et al. |
| 4,787,888 | A | 11/1988 | Fox |
| 4,826,494 | A | 5/1989 | Richmond et al. |
| 4,838,883 | A | 6/1989 | Matsuura |
| 4,840,187 | A | 6/1989 | Brazier |
| 4,863,449 | A | 9/1989 | Therriault et al. |
| 4,872,450 | A | 10/1989 | Austad |
| 4,878,901 | A | 11/1989 | Sachse |
| 4,897,081 | A | 1/1990 | Poirier et al. |
| 4,906,233 | A | 3/1990 | Moriuchi et al. |
| 4,906,240 | A | 3/1990 | Reed et al. |
| 4,919,654 | A | 4/1990 | Kalt |
| 4,941,882 | A | 7/1990 | Ward et al. |
| 4,953,565 | A | 9/1990 | Tachibana et al. |
| 4,969,880 | A | 11/1990 | Zamierowski |
| 4,985,019 | A | 1/1991 | Michelson |
| 5,037,397 | A | 8/1991 | Kalt et al. |
| 5,086,170 | A | 2/1992 | Luheshi et al. |
| 5,092,858 | A | 3/1992 | Benson et al. |
| 5,100,396 | A | 3/1992 | Zamierowski |
| 5,134,994 | A | 8/1992 | Say |
| 5,141,503 | A * | 8/1992 | Sewell, Jr. .......... A61M 1/0011 604/317 |
| 5,149,331 | A | 9/1992 | Ferdman et al. |
| 5,167,613 | A | 12/1992 | Karami et al. |
| 5,176,663 | A | 1/1993 | Svedman et al. |
| 5,215,522 | A | 6/1993 | Page et al. |
| 5,232,453 | A | 8/1993 | Plass et al. |
| 5,261,893 | A | 11/1993 | Zamierowski |
| 5,269,756 | A * | 12/1993 | Dryden .............. A61M 1/0058 128/207.16 |
| 5,278,100 | A | 1/1994 | Doan et al. |
| 5,279,550 | A | 1/1994 | Habib et al. |
| 5,298,015 | A | 3/1994 | Komatsuzaki et al. |
| 5,342,376 | A | 8/1994 | Ruff |
| 5,344,415 | A | 9/1994 | DeBusk et al. |
| 5,358,494 | A | 10/1994 | Svedman |
| 5,437,622 | A | 8/1995 | Carion |
| 5,437,651 | A | 8/1995 | Todd et al. |
| 5,527,293 | A | 6/1996 | Zamierowski |
| 5,549,584 | A | 8/1996 | Gross |
| 5,556,375 | A | 9/1996 | Ewall |
| 5,607,388 | A | 3/1997 | Ewall |
| 5,636,643 | A | 6/1997 | Argenta et al. |
| 5,645,081 | A | 7/1997 | Argenta et al. |
| 6,071,267 | A | 6/2000 | Zamierowski |
| 6,135,116 | A | 10/2000 | Vogel et al. |
| 6,241,747 | B1 | 6/2001 | Ruff |
| 6,287,316 | B1 | 9/2001 | Agarwal et al. |
| 6,345,623 | B1 | 2/2002 | Heaton et al. |
| 6,488,643 | B1 | 12/2002 | Tumey et al. |
| 6,493,568 | B1 | 12/2002 | Bell et al. |
| 6,553,998 | B2 | 4/2003 | Heaton et al. |
| 6,814,079 | B2 | 11/2004 | Heaton et al. |
| 7,846,141 | B2 | 12/2010 | Weston |
| 8,062,273 | B2 | 11/2011 | Weston |
| 8,216,198 | B2 | 7/2012 | Heagle et al. |
| 8,251,979 | B2 | 8/2012 | Malhi |
| 8,257,327 | B2 | 9/2012 | Blott et al. |
| 8,398,614 | B2 | 3/2013 | Blott et al. |
| 8,449,509 | B2 | 5/2013 | Weston |
| 8,529,548 | B2 | 9/2013 | Blott et al. |
| 8,535,296 | B2 | 9/2013 | Blott et al. |
| 8,551,060 | B2 | 10/2013 | Schuessler et al. |
| 8,568,386 | B2 | 10/2013 | Malhi |
| 8,679,081 | B2 | 3/2014 | Heagle et al. |
| 8,834,451 | B2 | 9/2014 | Blott et al. |
| 8,926,592 | B2 | 1/2015 | Blott et al. |
| 9,017,302 | B2 | 4/2015 | Vitaris et al. |
| 9,198,801 | B2 | 12/2015 | Weston |
| 9,211,365 | B2 | 12/2015 | Weston |
| 9,289,542 | B2 | 3/2016 | Blott et al. |
| 2002/0077661 | A1 | 6/2002 | Saadat |
| 2002/0115951 | A1 | 8/2002 | Norstrem et al. |
| 2002/0120185 | A1 | 8/2002 | Johnson |
| 2002/0143286 | A1 | 10/2002 | Tumey |
| 2010/0160871 | A1* | 6/2010 | Seegert .............. A61F 13/00063 604/290 |
| 2013/0066301 | A1* | 3/2013 | Locke .................. A61M 1/0049 604/543 |
| 2014/0163489 | A1* | 6/2014 | Walti .................. A61M 1/0054 604/319 |
| 2014/0163491 | A1 | 6/2014 | Schuessler et al. |
| 2015/0080788 | A1 | 3/2015 | Blott et al. |
| 2016/0015872 | A1 | 1/2016 | Luckemeyer et al. |
| 2016/0015873 | A1 | 1/2016 | Robinson et al. |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |

(56) References Cited

FOREIGN PATENT DOCUMENTS

| | | |
|---|---|---|
| EP | 0161865 A2 | 11/1985 |
| EP | 0358302 A2 | 3/1990 |
| EP | 1018967 A1 | 7/2000 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/020041 A1 | 9/1994 |
| WO | 96/05873 A1 | 2/1996 |
| WO | 97/18007 A1 | 5/1997 |
| WO | 99/13793 A1 | 3/1999 |
| WO | 2016040671 A1 | 3/2016 |

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.
Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al.; "Stimulation of Adenylate Cyclase Activity in Cultured Endothelial Cells Subjected to Cyclic Stretch"; Journal of Cardiovascular Surgery, 31, 1990, p. 634-639.
Orringer, Jay, et al.; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & dated Apr. 29, 1997.
PCT Written Opinion, PCT International Application PCT/GB96/02802; dated Sep. 3, 1997.
Dattillo, Philip P., Jr., et al.; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al.; "Vacuum Treatment in the Surgical Management of Purulent Wounds"; Vestnik Khirurgi, Sep. 1986, pp. 18-21 and 6 page English translation thereof.
Davydov, Yu. A., et al.; "Vacuum Therapy in the Treatment of Purulent Lactation Mastitis"; Vestnik Khirurgi, May 14, 1986, pp. 66-70, and 9 page English translation thereof.

Yusupov. Yun., et al.; "Active Wound Drainage", Vestnki Khirurgi, vol. 138, Issue 4, 1987, and 7 page English translation thereof.
Davydov, Yu.A., et al.; "Bacteriological and Cytological Assessment of Vacuum Therapy for Purulent Wounds" Vestnik Khirugi, Oct. 1988, pp. 48-52, and 8 page English translation thereof.
Davydov, Yu.A., et al.; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al.; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al.: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.A. Bagautdinov, "Vacuum and Vacuum-Sorption Treatment of Open Septic Wounds," in II All-Union Conference on Wounds and Wound Infections: Presentation Abstracts,

(56) References Cited

OTHER PUBLICATIONS edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C.® Therapy Clinical Guidelines: A Reference Source for Clinicians; Jul. 2007.

\* cited by examiner

NEGATIVE-PRESSURE THERAPY WITH DISPOSABLE INSTILLATION PUMP CHAMBER

RELATED APPLICATION

This application is a U.S. National Phase Entry of International Patent Application No. PCT/US2017/032917, filed May 16, 2017, which claims the benefit, under 35 USC § 119(e), of the filing of U.S. Provisional Patent Application Ser. No. 62/345,368, entitled "Negative-Pressure Therapy With Disposable Instillation Pump Chamber" filed Jun. 3, 2016, which is incorporated herein by reference for all purposes.

TECHNICAL FIELD

The invention set forth in the appended claims relates generally to tissue treatment systems and more particularly, but without limitation, to apparatuses and methods for providing negative-pressure therapy with instillation of topical treatment solutions.

BACKGROUND

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds or other tissue with reduced pressure may be commonly referred to as "negative-pressure therapy," but is also known by other names, including "negative-pressure wound therapy," "reduced-pressure therapy," "vacuum therapy," "vacuum-assisted closure," and "topical negative-pressure," for example. Negative-pres sure therapy may provide a number of benefits, including migration of epithelial and subcutaneous tissues, improved blood flow, and micro-deformation of tissue at a wound site. Together, these benefits can increase development of granulation tissue and reduce healing times.

There is also widespread acceptance that cleansing a tissue site can be highly beneficial for new tissue growth. For example, a wound can be washed out with a stream of liquid solution, or a cavity can be washed out using a liquid solution for therapeutic purposes. These practices are commonly referred to as "irrigation" and "lavage" respectively. "Instillation" is another practice that generally refers to a process of slowly introducing fluid to a tissue site and leaving the fluid for a prescribed period of time before removing the fluid. For example, instillation of topical treatment solutions over a wound bed can be combined with negative-pressure therapy to further promote wound healing by loosening soluble contaminants in a wound bed and removing infectious material. As a result, soluble bacterial burden can be decreased, contaminants removed, and the wound cleansed.

While the clinical benefits of negative-pressure therapy and instillation therapy are widely known, improvements to therapy systems, components, and processes may benefit healthcare providers and patients.

BRIEF SUMMARY

New and useful systems, apparatuses, and methods for instilling fluid to a tissue site in a negative-pressure therapy environment are set forth in the appended claims. Illustrative embodiments are also provided to enable a person skilled in the art to make and use the claimed subject matter. Some embodiments are illustrative of an apparatus or system for delivering therapeutic solution of fluids to a tissue site, which can be used in conjunction with negative-pressure therapy. For example, an apparatus may include a pneumatically-actuated instillation pump that can draw a solution from a solution source during a negative-pressure interval, and instill the solution to a dressing during a venting interval.

In some embodiments, for example, a pneumatic actuator may be mechanically coupled to a disposable distribution system. The distribution system may generally comprise a dosing chamber, and one or more fluid conductors that can provide a fluid path between the dosing chamber and a solution source, and between the dosing chamber and a distribution component, such as a dressing or dressing interface. One or more fluid conductors may also provide a fluid path between the actuator and a distribution component. A bacterial filter may be disposed in the fluid path between the actuator and the distribution component to prevent contamination of the actuator during operation. The distribution system may be separated from the actuator and disposed of after operation, and the actuator may be re-used.

More generally, some embodiments of an apparatus for managing fluid in a system for negative-pressure therapy may include a dosing chamber having a fluid inlet and a fluid outlet. A first check valve may be fluidly coupled to the fluid inlet, and a second check valve may be fluidly coupled to the fluid outlet. A fluid conductor can be fluidly coupled to the second check valve, and a fluid fitting can be fluidly coupled to the fluid conductor. A fluid port fluidly coupled to the fluid conductor can be configured to be coupled to a negative-pressure source, and a filter fluidly coupled to the fluid conductor between the fluid port and the fluid fitting can prevent contamination of other components. In some embodiments, the fluid conductor may comprise a constriction, and the filter is preferably a bacterial filter.

In more specific examples, the fluid port may comprise or consist essentially of a dressing pad configured to be coupled to a dressing, which can be applied to a tissue site. The fluid conductor may comprise a first conductor and a second conductor in some embodiments, and the fluid port can fluidly couple the first conductor to the second conductor. The apparatus may further include a liquid coupling, such as a spike connector, configured to couple the dosing chamber to a solution source. In some embodiments, the apparatus may additionally or alternatively include a solution source.

The apparatus may additionally include an instillation actuator in some embodiments. Such an instillation actuator may be fluidly coupled to the fluid fitting and mechanically coupled to the dosing chamber. The fluid coupling and the mechanical coupling are both preferably temporary couplings, adapted to allow the instillation actuator to be routinely coupled to and removed from the fluid fitting and the dosing chamber without compromising the integrity of any components. The instillation actuator may be configured to expand and contract the dosing chamber. For example, in some embodiments, the instillation actuator may comprise a piston chamber and a piston operably engaged to the dosing chamber. Pressure changes in the piston chamber can actuate the piston to expand and contract the dosing chamber. In some embodiments, expansion of the dosing chamber can draw solution into the dosing chamber, and contraction of the dosing chamber can expel the solution from the dosing chamber.

In some example embodiments, the apparatus may further comprise a negative-pressure source fluidly coupled to the fluid port. The negative-pressure source may provide negative-pressure intervals and venting intervals. In operation, the instillation actuator can expand the dosing chamber during a negative-pressure interval to draw a dose of solution from a solution source, and can contract the dosing chamber during a venting interval to expel the dose of solution from the dosing chamber to a dressing or other distribution component.

Alternatively, other example embodiments may include a system for providing negative-pressure and instillation therapy. The system may include a negative-pressure source configured to provide a negative-pressure interval and a venting interval, an actuator, and a distribution system. The actuator may comprise a pneumatic cylinder, and the distribution system may comprise a dosing chamber, a fluid port, and a fluid fitting in some embodiments. The fluid port may be configured to be fluidly coupled to the dosing chamber and to the negative-pressure source, and the fluid fitting can couple the pneumatic cylinder of the actuator to the fluid port. The actuator is preferably configured to expand the dosing chamber during the negative-pressure interval and contract the dosing chamber during the venting interval. In more specific examples, the distribution system may additionally include a bacterial filter between the fluid port and the fluid fitting.

A method for managing fluid in a therapy system may include fluidly coupling an apparatus or system as described to a dressing, which can be applied to a tissue site. Negative pressure may be applied to the tissue site for a first interval, in which instillation solution may be drawn into the dosing chamber. Negative pressure may be vented from the tissue site for a second interval, in which instillation solution can be delivered from the apparatus to the tissue site.

Objectives, advantages, and a preferred mode of making and using the claimed subject matter may be understood best by reference to the accompanying drawings in conjunction with the following detailed description of illustrative embodiments.

DESCRIPTION OF EXAMPLE EMBODIMENTS

The following description of example embodiments provides information that enables a person skilled in the art to make and use the subject matter set forth in the appended claims, but may omit certain details already well-known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive treatment. However, as should be recognized by those skilled in the art, this frame of reference is merely a descriptive expedient rather than a strict prescription.

Figure 1:
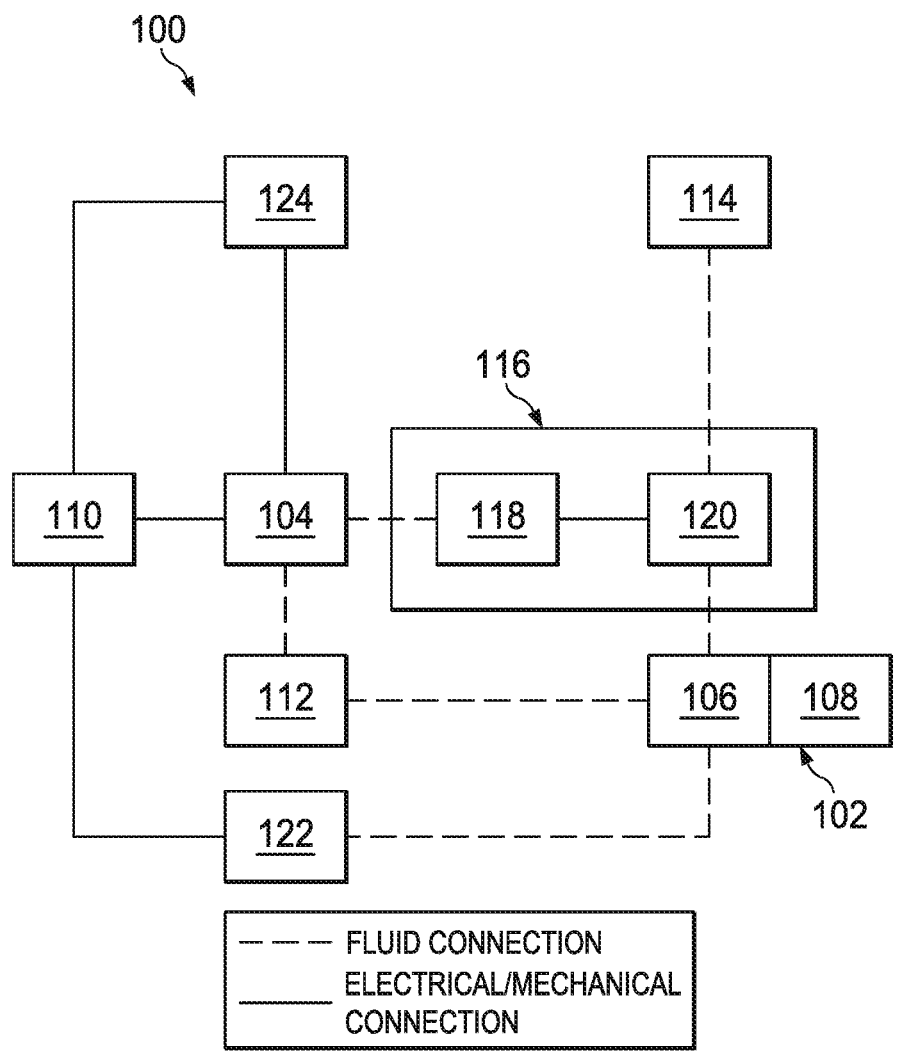
FIG. 1 is a functional block diagram of an example embodiment of a therapy system that can provide negative-pressure and instillation in accordance with this specification.

FIG. 1 is a simplified functional block diagram of an example embodiment of a therapy system 100 that can provide negative-pressure therapy with instillation of topical treatment solutions to a tissue site in accordance with this specification.

The term "tissue site" in this context broadly refers to a wound, defect, or other treatment target located on or within tissue, including but not limited to, bone tissue, adipose tissue, muscle tissue, neural tissue, dermal tissue, vascular tissue, connective tissue, cartilage, tendons, or ligaments. A wound may include chronic, acute, traumatic, subacute, and dehisced wounds, partial-thickness burns, ulcers (such as diabetic, pressure, or venous insufficiency ulcers), flaps, and grafts, for example. The term "tissue site" may also refer to areas of any tissue that are not necessarily wounded or defective, but are instead areas in which it may be desirable to add or promote the growth of additional tissue. For example, negative pressure may be applied to a tissue site to grow additional tissue that may be harvested and transplanted.

The therapy system 100 may include a negative-pressure supply, and may include or be configured to be coupled to a distribution component, such as a dressing. In general, a distribution component may refer to any complementary or ancillary component configured to be fluidly coupled to a negative-pressure supply between a negative-pressure supply and a tissue site. A distribution component is preferably detachable, and may be disposable, reusable, or recyclable. For example, a dressing 102 is illustrative of a distribution component fluidly coupled to a negative-pressure source 104 in FIG. 1. A dressing may include a cover, a tissue interface, or both in some embodiments. The dressing 102, for example, may include a cover 106 and a tissue interface 108. A regulator or a controller, such as a controller 110, may also be coupled to the negative-pressure source 104.

In some embodiments, another distribution component, such as a dressing interface, may facilitate coupling the negative-pressure source 104 to the dressing 102. For example, a dressing interface may be a T.R.A.C.® Pad or Sensa T.R.A.C.® Pad available from KCl of San Antonio, Tex. The therapy system 100 may optionally include a fluid container, such as a container 112, coupled to the dressing 102 and to the negative-pressure source 104.

The therapy system 100 may also include a source of installation solution, such as a solution source 114. A distribution component may be fluidly coupled to a fluid path between a solution source and a tissue site in some embodiments. For example, an installation pump 116 may be coupled to the solution source 114, as illustrated in the example embodiment of FIG. 1. In some embodiments, the installation pump 116 may comprise an actuator, such as an installation actuator 118, and a pump chamber, such as a dosing chamber 120. For example, the dosing chamber 120 may be fluidly coupled to the solution source 114 and to the dressing 102. The installation actuator 118 may be coupled to the dosing chamber 120 in some embodiments. In FIG. 1, for example, the installation actuator 118 may be mechanically coupled to the dosing chamber 120. The installation actuator 118 may also be fluidly coupled to the negative-pressure source 104. In some embodiments, the installation actuator 118 may be directly coupled to the negative-pressure source 104, as illustrated in FIG. 1, but may be indirectly coupled to the negative-pressure source 104 through other distribution components in some embodiments. For example, in some embodiments, the installation actuator 118 may be fluidly coupled to the negative-pressure source 104 through the dressing 102

Additionally, the therapy system 100 may include sensors to measure operating parameters and provide feedback signals to the controller 110 indicative of the operating parameters. As illustrated in FIG. 1, for example, the therapy system 100 may include a pressure sensor 122, an electric sensor 124, or both, coupled to the controller 110. The pressure sensor 122 may also be coupled or configured to be coupled to a distribution component and to the negative-pressure source 104.

Components may be fluidly coupled to each other to provide a distribution system for transferring fluids (i.e., liquid and/or gas). For example, a distribution system may include various combinations of fluid conductors and fittings to facilitate fluid coupling. A fluid conductor generally includes any structure with one or more lumina adapted to convey a fluid between two ends, such as a tube, pipe, hose, or conduit. Typically, a fluid conductor is an elongated, cylindrical structure with some flexibility, but the geometry and rigidity may vary. Some fluid conductors may be molded into or otherwise integrally combined with other components. A fitting can be used to mechanically and fluidly couple components to each other. For example, a fitting may comprise a projection and an aperture. The projection may be configured to be inserted into a fluid conductor so that the aperture aligns with a lumen of the fluid conductor. A valve is a type of fitting that can be used to control fluid flow. For example, a check valve can be used to substantially prevent return flow. A port is another example of a fitting. A port may also have a projection, which may be threaded, flared, tapered, barbed, or otherwise configured to provide a fluid seal when coupled to a component.

In some embodiments, components may also be coupled by virtue of physical proximity, being integral to a single structure, or being formed from the same piece of material. Coupling may also include mechanical, thermal, electrical, or chemical coupling (such as a chemical bond) in some contexts. For example, a tube may mechanically and fluidly couple the dressing 102 to the container 112 in some embodiments.

In general, components of the therapy system 100 may be coupled directly or indirectly. For example, the negative-pressure source 104 may be directly coupled to the controller 110, and may be indirectly coupled to the dressing 102 through the container 112.

The fluid mechanics of using a negative-pressure source to reduce pressure in another component or location, such as within a sealed therapeutic environment, can be mathematically complex. However, the basic principles of fluid mechanics applicable to negative-pressure therapy and instillation are generally well-known to those skilled in the art, and the process of reducing pressure may be described illustratively herein as "delivering," "distributing," or "generating" negative pressure, for example.

In general, exudates and other fluids flow toward lower pressure along a fluid path. Thus, the term "downstream" typically implies something in a fluid path relatively closer to a source of negative pressure or further away from a source of positive pressure. Conversely, the term "upstream" implies something relatively further away from a source of negative pressure or closer to a source of positive pressure. Similarly, it may be convenient to describe certain features in terms of fluid "inlet" or "outlet" in such a frame of reference. This orientation is generally presumed for purposes of describing various features and components herein. However, the fluid path may also be reversed in some applications (such as by substituting a positive-pressure source for a negative-pressure source) and this descriptive convention should not be construed as a limiting convention.

"Negative pressure" generally refers to a pressure less than a local ambient pressure, such as the ambient pressure in a local environment external to a sealed therapeutic environment provided by the dressing 102. In many cases, the local ambient pressure may also be the atmospheric pressure at which a tissue site is located. Alternatively, the pressure may be less than a hydrostatic pressure associated with tissue at the tissue site. Unless otherwise indicated, values of pressure stated herein are gauge pressures. Similarly, references to increases in negative pressure typically refer to a decrease in absolute pressure, while decreases in negative pressure typically refer to an increase in absolute pressure. While the amount and nature of negative pressure applied to a tissue site may vary according to therapeutic requirements, the pressure is generally a low vacuum, also commonly referred to as a rough vacuum, between −5 mm Hg (−667 Pa) and −500 mm Hg (−66.7 kPa). Common therapeutic ranges are between −75 mm Hg (−9.9 kPa) and −300 mm Hg (−39.9 kPa).

A negative-pressure supply, such as the negative-pressure source 104, may be a reservoir of air at a negative pressure, or may be a manual or electrically-powered device that can reduce the pressure in a sealed volume, such as a vacuum pump, a suction pump, a wall suction port available at many healthcare facilities, or a micro-pump, for example. A negative-pressure supply may be housed within or used in conjunction with other components, such as sensors, processing units, alarm indicators, memory, databases, software, display devices, or user interfaces that further facilitate therapy. For example, in some embodiments, the negative-pres sure source 104 may be combined with the controller 110 and other components into a therapy unit. A negative-pressure supply may also have one or more supply ports configured to facilitate coupling and de-coupling the negative-pressure supply to one or more distribution components.

The tissue interface 108 can be generally adapted to contact a tissue site. The tissue interface 108 may be partially or fully in contact with the tissue site. If the tissue site is a wound, for example, the tissue interface 108 may partially or completely fill the wound, or may be placed over the wound. The tissue interface 108 may take many forms, and may have many sizes, shapes, or thicknesses depending on a variety of factors, such as the type of treatment being implemented or the nature and size of a tissue site. For example, the size and shape of the tissue interface 108 may be adapted to the contours of deep and irregular shaped tissue sites. Moreover, any or all of the surfaces of the tissue interface 108 may have projections or an uneven, course, or jagged profile that can induce strains and stresses on a tissue site, which can promote granulation at the tissue site.

In some embodiments, the tissue interface 108 may be a manifold. A "manifold" in this context generally includes any substance or structure providing a plurality of pathways adapted to collect or distribute fluid across a tissue site under pressure. For example, a manifold may be adapted to receive negative pressure from a source and distribute negative pressure through multiple apertures across a tissue site, which may have the effect of collecting fluid from across a tissue site and drawing the fluid toward the source. In some embodiments, the fluid path may be reversed or a secondary fluid path may be provided to facilitate delivering fluid across a tissue site.

In some illustrative embodiments, the pathways of a manifold may be interconnected to improve distribution or collection of fluids across a tissue site. In some illustrative embodiments, a manifold may be a porous foam material having interconnected cells or pores. For example, cellular foam, open-cell foam, reticulated foam, porous tissue collections, and other porous material such as gauze or felted mat generally include pores, edges, and/or walls adapted to form interconnected fluid channels. Liquids, gels, and other foams may also include or be cured to include apertures and fluid pathways. In some embodiments, a manifold may additionally or alternatively comprise projections that form interconnected fluid pathways. For example, a manifold may be molded to provide surface projections that define interconnected fluid pathways.

The average pore size of a foam may vary according to needs of a prescribed therapy. For example, in some embodiments, the tissue interface 108 may be a foam having pore sizes in a range of 400-600 microns. The tensile strength of the tissue interface 108 may also vary according to needs of a prescribed therapy. For example, the tensile strength of a foam may be increased for instillation of topical treatment solutions. In one non-limiting example, the tissue interface 108 may be an open-cell, reticulated polyurethane foam such as GranuFoam® dressing or VeraFlo® foam, both available from Kinetic Concepts, Inc. of San Antonio, Tex.

The tissue interface 108 may be either hydrophobic or hydrophilic. In an example in which the tissue interface 108 may be hydrophilic, the tissue interface 108 may also wick fluid away from a tissue site, while continuing to distribute negative pressure to the tissue site. The wicking properties of the tissue interface 108 may draw fluid away from a tissue site by capillary flow or other wicking mechanisms. An example of a hydrophilic foam is a polyvinyl alcohol, open-cell foam such as V.A.C. WhiteFoam® dressing available from Kinetic Concepts, Inc. of San Antonio, Tex. Other hydrophilic foams may include those made from polyether. Other foams that may exhibit hydrophilic characteristics include hydrophobic foams that have been treated or coated to provide hydrophilicity.

The tissue interface 108 may further promote granulation at a tissue site when pressure within the sealed therapeutic environment is reduced. For example, any or all of the surfaces of the tissue interface 108 may have an uneven, coarse, or jagged profile that can induce microstrains and stresses at a tissue site if negative pressure is applied through the tissue interface 108.

In some embodiments, the tissue interface 108 may be constructed from bioresorbable materials. Suitable bioresorbable materials may include, without limitation, a polymeric blend of polylactic acid (PLA) and polyglycolic acid (PGA). The polymeric blend may also include without limitation polycarbonates, polyfumarates, and capralactones. The tissue interface 108 may further serve as a scaffold for new cell-growth, or a scaffold material may be used in conjunction with the tissue interface 108 to promote cell-growth. A scaffold is generally a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

In some embodiments, the cover 106 may provide a bacterial barrier and protection from physical trauma. The cover 106 may also be constructed from a material that can reduce evaporative losses and provide a fluid seal between two components or two environments, such as between a therapeutic environment and a local external environment. The cover 106 may be, for example, an elastomeric film or membrane that can provide a seal adequate to maintain a negative pressure at a tissue site for a given negative-pressure source. The cover 106 may have a high moisture-vapor transmission rate (MVTR) in some applications. For example, the MVTR may be at least 300 g/m^2 per twenty-four hours in some embodiments. In some example embodiments, the cover 106 may be a polymer drape, such as a polyurethane film, that is permeable to water vapor but impermeable to liquid. Such drapes typically have a thickness in the range of 25-50 microns. For permeable materials, the permeability generally should be low enough that a desired negative pressure may be maintained.

An attachment device may be used to attach the cover 106 to an attachment surface, such as undamaged epidermis, a gasket, or another cover. The attachment device may take many forms. For example, an attachment device may be a medically-acceptable, pressure-sensitive adhesive that extends about a periphery, a portion, or an entire sealing member. In some embodiments, for example, some or all of the cover 106 may be coated with an acrylic adhesive having a coating weight between 25-65 grams per square meter (g.s.m.). Thicker adhesives, or combinations of adhesives, may be applied in some embodiments to improve the seal and reduce leaks. Other example embodiments of an attachment device may include a double-sided tape, paste, hydrocolloid, hydrogel, silicone gel, or organogel.

A controller, such as the controller 110, may be a microprocessor or computer programmed to operate one or more components of the therapy system 100, such as the negative-pressure source 104. In some embodiments, for example, the controller 110 may be a microcontroller, which generally comprises an integrated circuit containing a processor core and a memory programmed to directly or indirectly control one or more operating parameters of the therapy system 100. Operating parameters may include the power applied to the negative-pressure source 104, the pressure generated by the negative-pressure source 104, or the pressure distributed to the tissue interface 108, for example. The controller 110 is also preferably configured to receive one or more input signals, such as a feedback signal, and programmed to modify one or more operating parameters based on the input signals.

Sensors, such as the pressure sensor 122 or the electric sensor 124, are generally known in the art as any apparatus operable to detect or measure a physical phenomenon or property, and generally provide a signal indicative of the phenomenon or property that is detected or measured. For example, the pressure sensor 122 and the electric sensor 124 may be configured to measure one or more operating parameters of the therapy system 100. In some embodiments, the pressure sensor 122 may be a transducer configured to measure pressure in a pneumatic pathway and convert the measurement to a signal indicative of the pressure measured. In some embodiments, for example, the pressure sensor 122 may be a piezoresistive strain gauge. The electric sensor 124 may optionally measure operating parameters of the negative-pressure source 104, such as the voltage or current, in some embodiments. Preferably, the signals from the pressure sensor 122 and the electric sensor 124 are suitable as an input signal to the controller 110, but some signal conditioning may be appropriate in some embodiments. For example, the signal may need to be filtered or amplified before it can be processed by the controller 110. Typically, the signal is an electrical signal, but may be represented in other forms, such as an optical signal.

The container 112 is representative of a container, canister, pouch, or other storage component, which can be used to manage exudates and other fluids withdrawn from a tissue site. In many environments, a rigid container may be preferred or required for collecting, storing, and disposing of fluids. In other environments, fluids may be properly disposed of without rigid container storage, and a re-usable container could reduce waste and costs associated with negative-pressure therapy.

The solution source 114 may also be representative of a container, canister, pouch, bag, or other storage component, which can provide a solution for instillation therapy. Compositions of solutions may vary according to a prescribed therapy, but examples of solutions that may be suitable for some prescriptions include hypochlorite-based solutions, silver nitrate (0.5%), sulfur-based solutions, biguanides, cationic solutions, and isotonic solutions.

In operation, the tissue interface 108 may be placed within, over, on, or otherwise proximate to a tissue site. The cover 106 may be placed over the tissue interface 108 and sealed to an attachment surface near the tissue site. For example, the cover 106 may be sealed to undamaged epidermis peripheral to a tissue site. Thus, the dressing 102 can provide a sealed therapeutic environment proximate to a tissue site, substantially isolated from the external environment, and the negative-pressure source 104 can reduce the pressure in the sealed therapeutic environment. Negative pressure applied across the tissue site through the tissue interface 108 in the sealed therapeutic environment can induce macrostrain and microstrain in the tissue site, as well as remove exudates and other fluids from the tissue site, which can be collected in container 112. In some embodiments, negative pressure may be applied intermittently or periodically, with intervals of negative pressure and intervals of venting or positive pressure.

During negative-pressure intervals, negative pressure can actuate the instillation actuator 118, which can operate the dosing chamber 120. For example, in some embodiments, the instillation actuator 118 can expand the dosing chamber 120 during a negative-pressure interval, lowering pressure in the dosing chamber 120 and drawing instillation solution into the dosing chamber 120 from the solution source 114 through a first check valve, which can substantially prevent return of the instillation solution from the dosing chamber 120 to the solution source 114. During a subsequent venting interval, the instillation actuator 118 can contract the dosing chamber 120, increasing the pressure in the dosing chamber 120 and expelling instillation solution from the dosing chamber 120 through a second check valve to the dressing 102. The second check valve can substantially prevent return of the instillation solution (as well as exudate) to the dosing chamber 120. The instillation solution may dwell at the tissue site for the duration of the venting interval, and then be removed from the tissue site and drawn into the container 112 during a subsequent negative-pressure interval. A filter can be disposed between the instillation actuator 118 and the dressing 102 to prevent contamination of the instillation actuator 118. For example, the filter may be a bacterial filter configured to remove bacteria from fluid flowing through the filter from the dressing 102.

Figure 2:
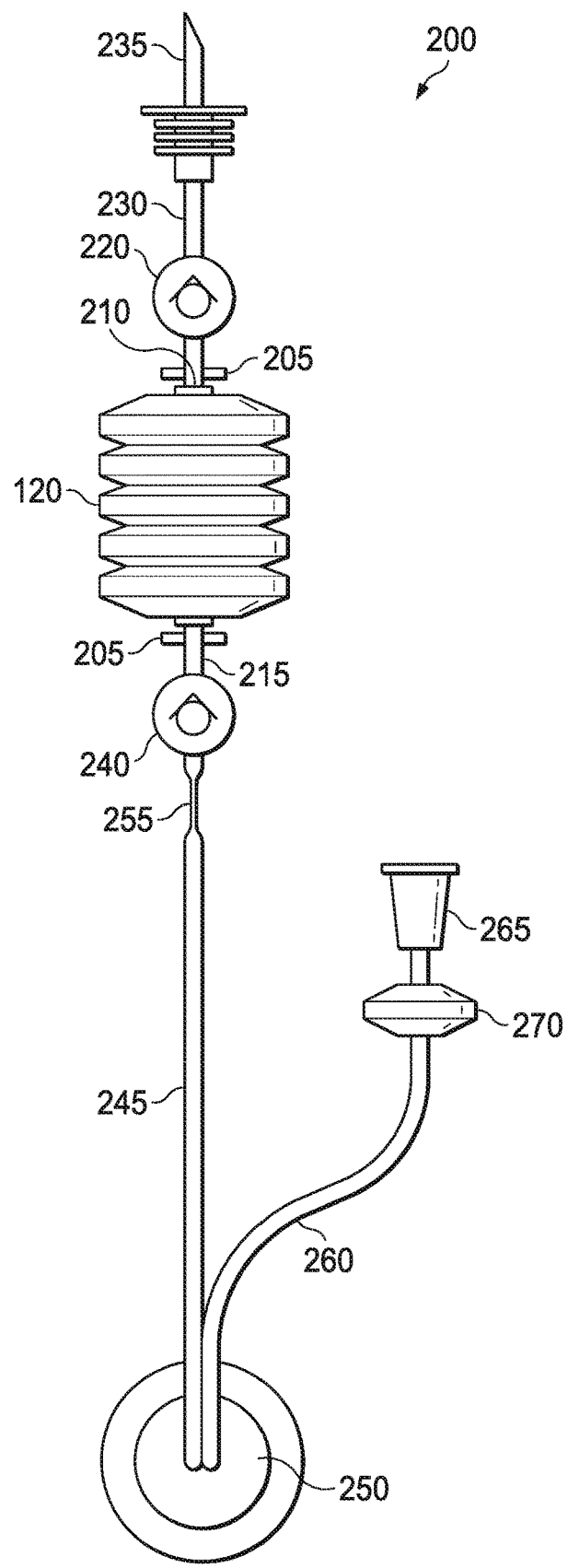
FIG. 2 is a schematic diagram illustrating additional details of a distribution system that may be associated with some example embodiments of the therapy system of FIG. 1.

FIG. 2 is a schematic diagram illustrating additional details of a distribution system 200 that may be associated with some example embodiments of the instillation pump 116. In the example embodiment of FIG. 2, the dosing chamber 120 may be a bellows, flexible bladder, or other chamber with flexible side walls suitable for holding instillation solution. In other example embodiments, the dosing chamber 120 may comprise a rigid wall with a reciprocating piston. The dosing chamber 120 of FIG. 2 generally comprises opposing fixation points 205, a fluid inlet 210, and a fluid outlet 215.

As illustrated in FIG. 2, a first check valve 220 may be fluidly coupled to the fluid inlet 210. The first check valve 220 may be fluidly coupled to a first fluid conductor 230. An interface 235 may also be coupled to the first fluid conductor 230 in some embodiments. The interface 235 is generally configured to connect the first fluid conductor 230 to a solution source, such as the solution source 114. For example, in some embodiments, the interface 235 may be a connector configured to puncture a bag or port, such as a spike connector. In other embodiments, the first fluid conductor 230 may be directly coupled to the solution source 114.

The fluid outlet 215 may be fluidly coupled to a second check valve 240, which may be fluidly coupled to a second fluid conductor 245. The second fluid conductor 245 may be fluidly coupled to a fluid port 250 in some embodiments. In some embodiments, the second fluid conductor 245 may have a constriction 255 between the second check valve 240 and the fluid port 250.

The fluid port 250 is generally configured to fluidly couple the second fluid conductor 245 to another distribution component, such as the dressing 102. For example, the fluid port 250 may be a dressing interface, or may be configured to be coupled to a dressing interface in some embodiments.

A third fluid conductor 260 may also be fluidly coupled to the fluid port 250. In some embodiments, the third fluid conductor 260 may be directly coupled to the fluid port 250, as illustrated in the example of FIG. 2. In other embodiments, the third fluid conductor 260 may be indirectly coupled to the fluid port 250. For example, the third fluid conductor 260 may be fluidly coupled to the second fluid conductor 245, which can indirectly couple the third fluid conductor 260 to the fluid port 250. In yet other examples, the distribution system may comprise a second fluid port, and the third fluid conductor 260 may be fluidly coupled to the second fluid port.

A fluid fitting 265 can be coupled to the third fluid conductor 260 opposite the fluid port 250. The fluid fitting 265 is generally configured to fluidly couple the third fluid conductor 260 to an instillation actuator, such as the instillation actuator 118. A bacterial filter 270 can also be coupled to the third fluid conductor 260 between the fluid port 250 and the fluid fitting 265.

Figure 3A:
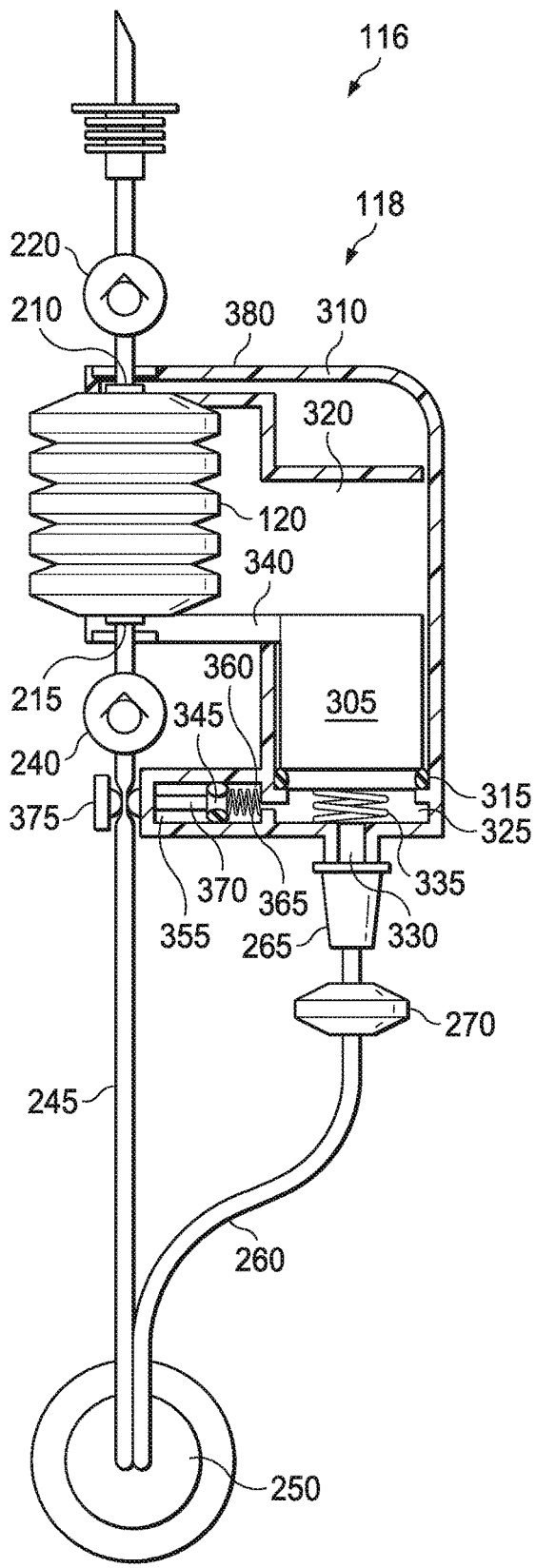
FIG. 3A is a schematic diagram illustrating additional details that may be associated with some embodiments of an instillation pump during a negative-pressure interval.
Figure 3B:
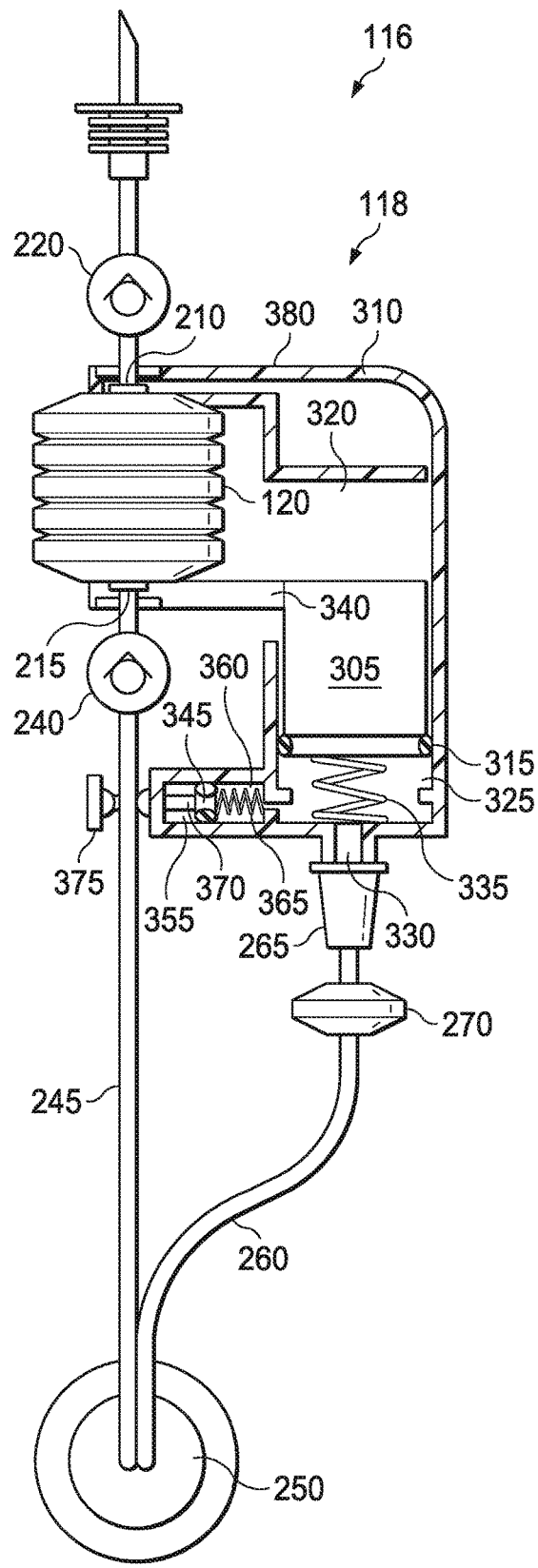
FIG. 3B is a schematic diagram illustrating additional details that may be associated with some embodiments of an instillation pump during a venting interval.

FIG. 3A is a schematic diagram illustrating additional details that may be associated with some embodiments of the instillation pump 116 during a negative-pressure interval. FIG. 3B is a schematic diagram illustrating additional details that may be associated with some embodiments of the instillation pump 116 during a venting interval. FIG. 3A and FIG. 3B also illustrate an example embodiment of the instillation actuator 118 operatively coupled to the distribution system 200 of FIG. 2.

The instillation actuator 118 may comprise one or more pneumatic cylinders in some embodiments. In general, a pneumatic cylinder may comprise a piston contained within a piston chamber of a housing. The piston may be a disc, cylinder, diaphragm, or other working member that can provide a fluid barrier, and pressure changes in the piston chamber may move the piston within the piston chamber. Movement within the chamber is typically a rectilinear motion between two opposing extremities. A pneumatic cylinder also generally includes a low-friction fluid seal between the piston and side walls of the piston chamber. The fluid seal may be attached to the side walls of the piston chamber, allowing relative movement between the piston and the fluid seal, or the fluid seal may be attached to the piston, allowing relative movement between the fluid seal and the piston chamber. The fluid seal and the piston effectively partition the piston chamber into a working chamber and an ambient chamber. The working chamber can be fluidly coupled to a fluid port in the housing, through which a working fluid can be transferred to and from the working chamber. In some embodiments, a pneumatic cylinder may also include a spring return to bias the piston to a neutral position. For example, a spring may be coupled to the piston in the working chamber, the ambient chamber, or both.

For example, as illustrated in the example of FIG. 3A and FIG. 3B, some embodiments of the instillation actuator 118 may comprise a dosing piston 305 contained within a piston chamber of a housing 310. A seal 315 can partition the piston chamber into an ambient chamber 320 and a working chamber 325. A fluid port 330 may be fluidly coupled to the working chamber 325. In some embodiments, a return spring 335 may also be disposed in the working chamber 325 and coupled to a first side of the dosing piston 305. The dosing piston 305 may also be coupled to or otherwise comprise a dosing rod 340 coupled to a second side. A working fluid entering the working chamber 325 through the fluid port 330 can cause pressure changes in the working chamber 325 and a resulting movement of the dosing piston 305 between a first position and a second position.

In some embodiments, the instillation actuator 118 may additionally comprise a clamping piston 345, and the housing 310 may further comprise or define a second piston chamber in which the clamping piston 345 may be disposed. A second low-friction seal 350 may be disposed in the second piston chamber between the housing 310 and the clamping piston 345, dividing the second piston chamber into an ambient chamber 355 and a working chamber 360. The working chamber 360 may be fluidly coupled to the fluid port 330 in some embodiments. For example, the working chamber 360 may be fluidly coupled to the fluid port 330 through the working chamber 325, as illustrated in the example of FIG. 3A and FIG. 3B. In other embodiments, the working chamber 360 may be fluidly coupled to a second fluid port. In some embodiments, a return spring 365 may be disposed in the working chamber 360 and coupled to a first side of the clamping piston 345. A clamping rod 370 may be coupled to a second side of the clamping piston 345. The clamping rod 370 may pass through the housing 310 and be coupled to a clamp 375 outside the housing 310. The clamp 375 generally has an open state and a closed state. A working fluid entering the working chamber 360 through the fluid port 330 can cause pressure changes in the working chamber 360 and a resulting movement of the clamping piston 345 between a first position and a second position. The movement of the clamping piston 345 can be transferred to the clamp 375 through the clamping rod 370, opening and closing the clamp 375. For example, the first position of the clamping piston 345 may correspond to the closed state of the clamp 375 and the second position of the clamping piston 345 may correspond to the open state of the clamp 375.

The instillation actuator 118 may be fastened to the distribution system 200. For example, some embodiments of the instillation actuator 118 may comprise one or more attachment arms, such as an attachment arm 380, which can be releasably fastened to the distribution system 200. In some embodiments, a first end of the attachment arm 380 may be rigidly coupled to the housing 310. As illustrated in the example of FIG. 3A and FIG. 3B, a second end of the attachment arm 380 may be fastened to the dosing chamber 120 adjacent to the fluid inlet 210. The instillation actuator 118 or the attachment arm 380 preferably comprises one or more fasteners, which can be readily coupled to and uncoupled from the distribution system 200 without compromising the integrity of the instillation actuator 118 or the distribution system 200. Suitable fasteners may include retaining rings, snap rings, or terry clips, for example. In some embodiments, the fastener may be configured to attach directly to the dosing chamber 120, and relative motion between the dosing chamber 120 and the housing 310 may additionally be constrained by a fixation point 205.

The dosing piston 305 may be similarly fastened to the distribution system 200. For example, in the example embodiment of FIG. 3A and FIG. 3B, the dosing rod 340 of the dosing piston 305 may be fastened to the dosing chamber 120 adjacent to the fluid outlet 215.

The clamp 375 may be also be operably coupled to the distribution system 200 in some embodiments. For example, the second fluid conductor 245 may be positioned within or through the clamp 375. In some examples, the fluid constriction 255 may be positioned within or through the clamp 375, and the clamp 375 may be supported from above or below by suitable fasteners.

The fluid port 330 may be fluidly coupled to the fluid port 250. For example, the fluid fitting 265 may be coupled to the fluid port 330, providing a fluid path between the fluid port 330 and the fluid port 250 through the third fluid conductor 260.

In operation, the fluid port 250 may also be fluidly coupled to a negative-pressure source, such as the negative-pressure source 104, and the fluid inlet 210 may be fluidly coupled to a source of instillation solution, such as the solution source 114. In some embodiments the fluid port 250 may be indirectly coupled to a negative-pressure source through other distribution components, such as a dressing. For example, the fluid port 250 may be coupled to the dressing 102.

During a negative-pressure interval, negative pressure applied to the fluid port 250 may be distributed to the fluid outlet 215 and to the fluid port 330. A fluid constriction, such as the fluid constriction 255, between the fluid outlet 215 and the fluid port 250 can allow pressure in the working chamber 360 to decrease at a faster rate than pressure in the dosing chamber 120.

If negative pressure in the working chamber 360 exceeds a first negative-pressure threshold, the pressure differential across the clamping piston 345 can overcome the force of the return spring 365, moving the clamping piston 345 to compress the return spring 365 in the working chamber 360 as illustrated in the example of FIG. 3A. Movement of the clamping piston 345 may be transferred to the clamp 375 through the clamping rod 370, closing the clamp 375 on the second fluid conductor 245, also illustrated in the example of FIG. 3A. In the closed state, the clamp 375 preferably prevents fluid transfer between the dosing chamber 120 and the fluid port 250 through the second fluid conductor 245.

If negative pressure in the working chamber 325 exceeds a second negative-pressure threshold, the pressure differential across the dosing piston 305 can overcome the force of the return spring 335, moving the dosing piston 305 to compress the return spring 335 in the working chamber 325 as illustrated in the example of FIG. 3A. In some embodiments, the second negative-pressure threshold may be greater than the first negative-pressure threshold, so that the clamp 375 can be closed before the dosing piston 305 moves. In other example embodiments, the second negative-pressure threshold may be substantially equal to the first negative-pressure threshold. Movement of the dosing piston 305 may be transferred to the dosing chamber 120. For example, the dosing piston 305 may move the dosing rod 340. If the fluid inlet 210 is held static by the attachment arm 380 coupled to the adjacent fixation point 205, as in the example of FIG. 3A, movement of the dosing rod 340 can move the fluid outlet 215 relative to the fluid inlet 210, expanding the working volume of the dosing chamber 120, as also illustrated in the example of FIG. 3A.

The second check valve 240 may be normally closed, creating a closed system of the solution source 114 and the dosing chamber 120. Expansion of the dosing chamber 120 reduces the pressure in the dosing chamber under such conditions, creating a pressure gradient between the solution source 114 and the dosing chamber 120 that can move instillation solution from the solution source 114 through the first check valve 220 into the dosing chamber 120. Additionally or alternatively, in some example configurations gravity may also move instillation solution from the solution source 114 into the dosing chamber 120, particularly if the solution source 114 is elevated above the dosing chamber 120.

The amount of fluid transferred from the solution source 114 to the dosing chamber 120 can be calibrated by modifying certain system parameters. For example, the size of the piston chamber or the spring constant of the return spring 335 can be modified to change the stroke length of the dosing piston 305 in some embodiments. Alternatively or additionally, the size of the dosing chamber 120 may be increased or decreased according to therapeutic needs. In yet other examples, the dosing may be controlled or modified by the controller 110. For example, the controller 110 may be programmed to change the frequency or duration of venting intervals or negative-pressure intervals, or both, which can control dosing and the dwell time of instillation fluid.

During a venting interval, negative pressure in the working chamber 360 can decrease until clamp 375 opens, as illustrated in the example of FIG. 3B. For example, if the first negative-pressure threshold exceeds the negative pressure in the working chamber 360, the force of the return spring 365 can overcome the pressure differential across the clamping piston 345, allowing the clamping piston 345 to return to a neutral position and opening the clamp 375.

If the second negative-pressure threshold exceeds the negative pressure in the working chamber 325, the force of the return spring 335 can exceed the pressure differential across the dosing piston 305, allowing the dosing piston 305 return to a neutral position, as illustrated in the example of FIG. 3B. Movement of the dosing piston 305 to the neutral position may be transferred to the dosing chamber 120. For example, the dosing piston 305 may move the dosing rod 340. If the fluid inlet 210 is held static by the attachment arm 380 coupled to the adjacent fixation point 205, as in the example of FIG. 3B, movement of the dosing rod 340 can move the fluid outlet 215 relative to the fluid inlet 210, contracting the working volume of the dosing chamber 120, as also illustrated in the example of FIG. 3B.

The first check valve 220 may be normally closed, and contracting the dosing chamber 120 can increase the pressure in the dosing chamber 120 under such conditions, creating a pressure gradient between the dosing chamber 120 and the fluid port 250 that can move instillation solution from the dosing chamber 120 through the second check valve 240 into the second fluid conductor 245. The first check valve 220 can prevent instillation solution from being returned to the solution source 114 as the pressure increases. In some embodiments, the instillation solution can be delivered to the dressing 102 through the fluid port 250. Instillation solution may also be transferred from the second fluid conductor 245 to the third fluid conductor in some embodiments. For example, a large dose of instillation solution may be at least partially (and temporarily) transferred to the fluid conductor 260 if the dose exceeds the capacity of the dressing 102. The bacterial filter 270 can prevent contamination of the instillation actuator 118.

Figure 4:
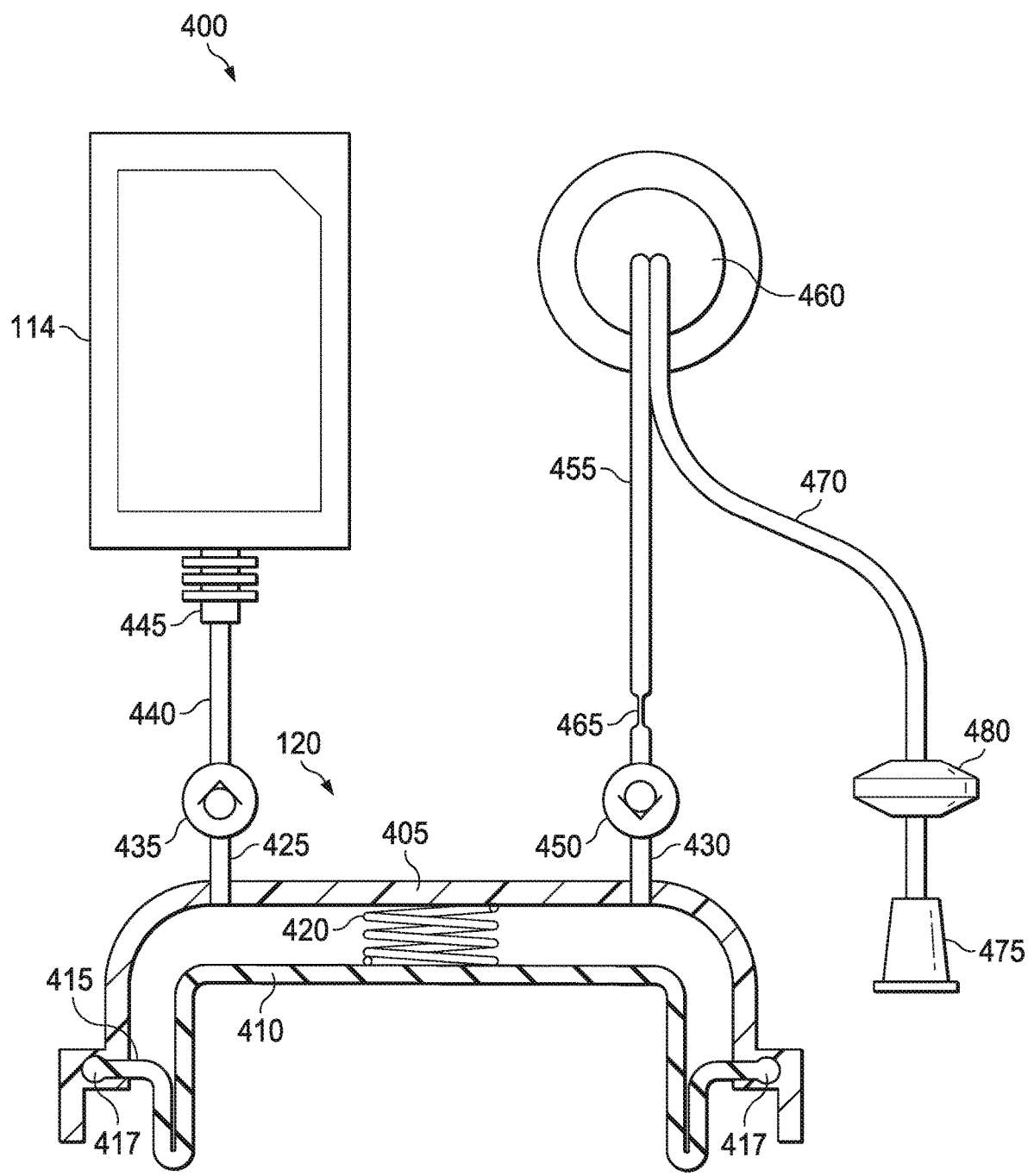
FIG. 4 is a schematic diagram illustrating additional details of another example distribution system that may be associated with some embodiments of the therapy system of FIG. 1.

FIG. 4 is a schematic diagram illustrating additional details of another example distribution system 400 that may be associated with some embodiments of the instillation pump 116. In the example embodiment of FIG. 4, the dosing chamber 120 may comprise a housing and a rolling diaphragm or other flexible barrier. For example, as illustrated in the embodiment of FIG. 4, the dosing chamber 120 may comprise a housing 405 and a rolling diaphragm 410. In some embodiments, the housing 405 may be a half-cylinder, and is preferably sufficiently rigid to maintain its shape in operation. The rolling diaphragm 410 may comprise a flange 415, which can be coupled to the housing 405 to provide a seal across the housing 405, defining a pressure vessel having a variable volume and flexible, moving side-walls. The dosing chamber 120 may additionally comprise one or more fixation points 417, a return spring 420, a fluid inlet 425, and a fluid outlet 430.

As illustrated in FIG. 4, a first check valve 435 may be fluidly coupled to the fluid inlet 425. The first check valve 435 may be fluidly coupled to a first fluid conductor 440. An interface 445 may also be coupled to the first fluid conductor 440 in some embodiments. The interface 445 is generally configured to connect the first fluid conductor 440 to a solution source, such as the solution source 114. For example, in some embodiments, the interface 445 may be a connector configured to puncture a bag or port, such as a spike connector. In other embodiments, the first fluid conductor 440 may be directly coupled to the solution source 114.

The fluid outlet 430 may be fluidly coupled to a second check valve 450, which may be fluidly coupled to a second fluid conductor 455. The second fluid conductor 455 may be fluidly coupled to a fluid port 460 in some embodiments. In some embodiments, the second fluid conductor 455 may have a constriction 465 between the second check valve 450 and the fluid port 460.

The fluid port 460 is generally configured to fluidly couple the second fluid conductor 455 to another distribution component, such as the dressing 102. For example, the fluid port 460 may be a dressing interface, or may be configured to be coupled to a dressing interface in some embodiments.

A third fluid conductor 470 may also be fluidly coupled to the fluid port 460. In some embodiments, the third fluid conductor 470 may be directly coupled to the fluid port 460, as illustrated in the example of FIG. 4. In other embodiments, the third fluid conductor 470 may be indirectly coupled to the fluid port 460. For example, the third fluid conductor 470 may be fluidly coupled to the second fluid conductor 455, which can indirectly couple the third fluid conductor 470 to the fluid port 460.

A fluid fitting 475 can be coupled to the third fluid conductor 470 opposite the fluid port 460. The fluid fitting 475 is generally configured to fluidly couple the third fluid conductor 470 to an instillation actuator, such as the instillation actuator 118. A bacterial filter 480 can also be coupled to the third fluid conductor 470 between the fluid port 460 and the fluid fitting 475.

In some embodiments, the dosing chamber 120 may additionally include a biasing element, such as the return spring 420, disposed between the housing 405 and the rolling diaphragm 410 to bias the rolling diaphragm 410 away from the housing 405.

Figure 5A:
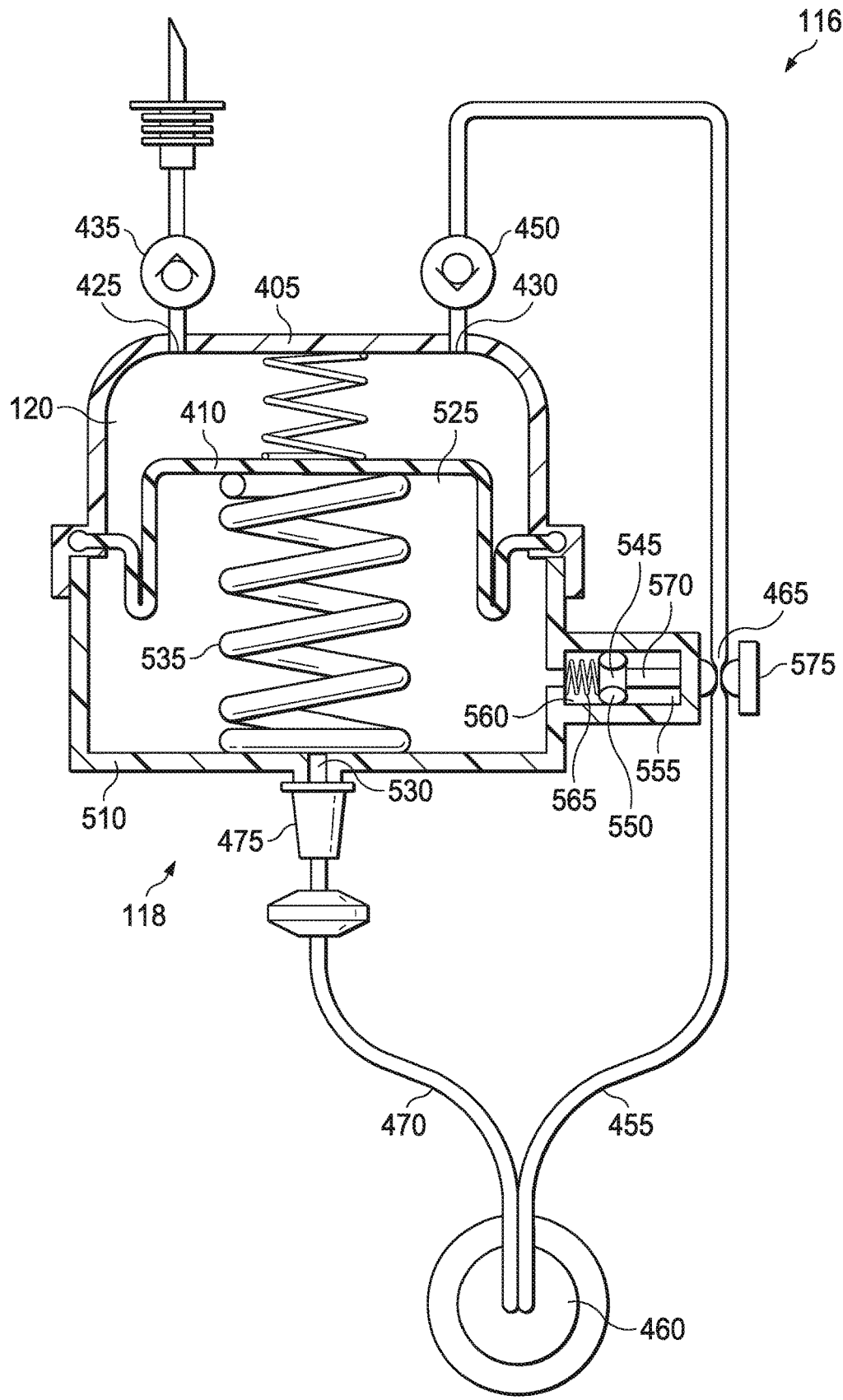
FIG. 5A is a schematic diagram illustrating additional details that may be associated with other example embodiments of an instillation pump during a negative-pressure interval.
Figure 5B:
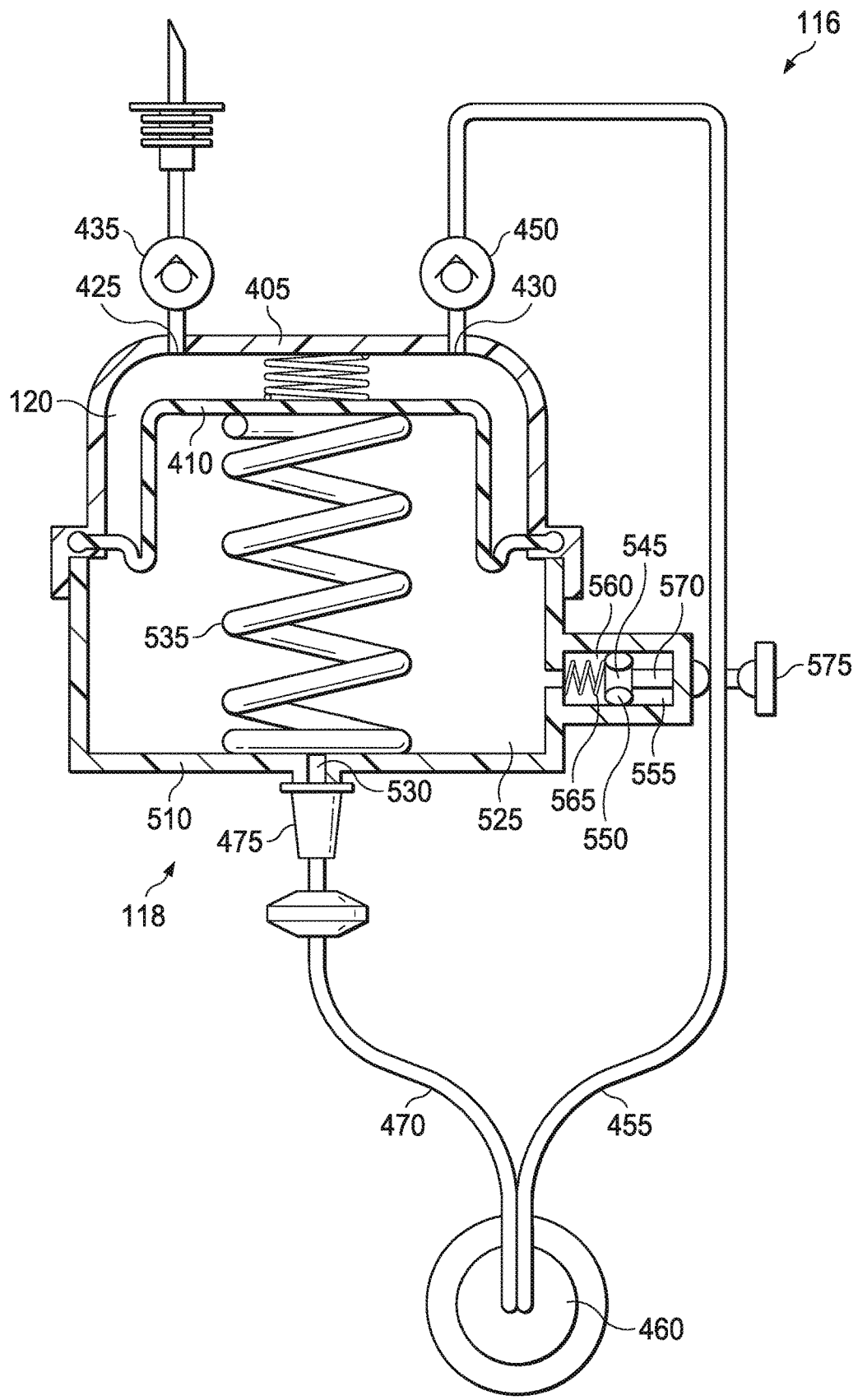
FIG. 5B is a schematic diagram illustrating additional details that may be associated with other example embodiments of an instillation pump during a venting interval.

FIG. 5A is a schematic diagram illustrating additional details that may be associated with other example embodiments of the instillation pump 116 during a negative-pressure interval. FIG. 5B is a schematic diagram illustrating additional details that may be associated with other example embodiments of the instillation pump 116 during a venting interval. FIG. 5A and FIG. 5B also illustrate another example embodiment of the instillation actuator 118, operatively coupled to the distribution system 400 of FIG. 4.

The example instillation actuator 118 of FIG. 5A and FIG. 5B may also comprise one or more pneumatic cylinders in some embodiments. For example, some embodiments of the instillation actuator 118 may comprise a housing 510 that can be coupled to the housing 405, and the diaphragm 410 can partition the dosing chamber 120 from a working chamber 525 between the housing 510 and the diaphragm 410. In some embodiments, the instillation actuator 118 may additionally comprise a piston (not shown) operably engaged to the diaphragm 410, but the diaphragm 410 may effectively operate as a piston in some embodiments. For example, the diaphragm 410 may be sufficiently flexible to move under the influence of a pressure differential across it, or may be directly engaged to a return spring 535, as shown in the example of FIG. 5A and FIG. 5B.

A fluid port 530 may be fluidly coupled to the working chamber 525. A working fluid entering the working chamber 525 through the fluid port 530 can cause pressure changes in the working chamber 525 and a resulting movement of the diaphragm 410 between a first position and a second position.

In some embodiments, the instillation actuator 118 may additionally comprise a clamping piston 545, and the housing 510 may further comprise or define a second piston chamber in which the clamping piston 545 may be disposed.

A low-friction seal 550 may be disposed in the second piston chamber between the housing 510 and the clamping piston 545, dividing the second piston chamber into an ambient chamber 555 and a working chamber 560. The working chamber 560 may be fluidly coupled to the fluid port 530 in some embodiments. For example, the working chamber 560 may be fluidly coupled to the fluid port 530 through the working chamber 525, as illustrated in the example of FIG. 5A and FIG. 5B. In other embodiments, the working chamber 560 may be fluidly coupled to a second fluid port. In some embodiments, a return spring 565 may be disposed in the working chamber 560 and coupled to a first side of the clamping piston 545. A clamping rod 570 may be coupled to a second side of the clamping piston 545. The clamping rod 570 may pass through the housing 510 and be coupled to a clamp 575 outside the housing 510. The clamp 575 generally has an open state and a closed state. A working fluid entering the working chamber 560 through the fluid port 530 can cause pressure changes in the working chamber 560 and a resulting movement of the clamping piston 545 between a first position and a second position. The movement of the clamping piston 545 can be transferred to the clamp 575 through the clamping rod 570, opening and closing the clamp 575. For example, the first position of the clamping piston 545 may correspond to the closed state of the clamp 575 and the second position of the clamping piston 545 may correspond to the open state of the clamp 575.

The instillation actuator 118 may be operably coupled to the distribution system 400. Some embodiments of the housing 510 may comprise one or more fasteners, which can be releasably fastened to the distribution system 400. For example, the housing 510 may be configured to be threaded onto the dosing chamber 120 in some embodiments. Additionally or alternatively, the instillation actuator 118 may comprise one or more fasteners, which can be readily coupled to and uncoupled from the dosing chamber 120 without compromising the integrity of the instillation actuator 118 or the dosing chamber 120. Suitable fasteners may include retaining rings, snap rings, or terry clips, for example.

The clamp 575 may be also be operably coupled to the distribution system 400 in some embodiments. For example, the second fluid conductor 455 may be positioned within or through the clamp 575. In some examples, the fluid constriction 465 may be positioned within or through the clamp 575, and the clamp 575 may be supported from above or below by suitable fasteners.

The fluid port 530 may be fluidly coupled to the fluid port 460. For example, the fluid fitting 475 may be coupled to the fluid port 530, providing a fluid path between the fluid port 530 and the fluid port 460 through the third fluid conductor 470.

In operation, the fluid port 460 may also be fluidly coupled to a negative-pressure source, such as the negative-pressure source 104, and the fluid inlet 425 may be fluidly coupled to a source of instillation solution, such as the solution source 114. In some embodiments the fluid port 460 may be indirectly coupled to a negative-source through other distribution components, such as a dressing. For example, the fluid port 460 may be coupled to the dressing 102.

During a negative-pressure interval, negative pressure applied to the fluid port 460 may be distributed to the fluid outlet 430 and to the fluid port 530. A fluid constriction, such as the fluid constriction 465, between the fluid outlet 430 and the fluid port 460 can allow pressure in the working chamber 525 to decrease at a faster rate than pressure in the dosing chamber 120.

If negative pressure in the working chamber 560 exceeds a first negative-pressure threshold, the pressure differential across the clamping piston 545 can overcome the force of the return spring 565, moving the clamping piston 545 to compress the return spring 565 in the working chamber 560 as illustrated in the example of FIG. 5A. Movement of the clamping piston 545 may be transferred to the clamp 575 through the clamping rod 570, closing the clamp 575 on the second fluid conductor 455, also illustrated in the example of FIG. 5A. In the closed state, the clamp 575 preferably prevents fluid transfer between the dosing chamber 120 and the fluid port 460 through the second fluid conductor 455. The first position and the second position of the claim 575 may vary, depending on the diameter and wall thickness of the second fluid conductor 455, for example.

If negative pressure in the working chamber 525 exceeds a second negative-pressure threshold, the pressure differential across the diaphragm 410 can overcome the force of the return spring 535, moving the diaphragm 410 to compress the return spring 535 in the working chamber 525 as illustrated in the example of FIG. 5A. In some embodiments, the second negative-pressure threshold may be greater than the first negative-pressure threshold, so that the clamp 575 can be closed before the diaphragm 410 moves. In other example embodiments, the second negative-pressure threshold may be substantially equal to the first negative-pressure threshold. Movement of the diaphragm 410 against the return spring 535 can also expand the working volume of the dosing chamber 120, as also illustrated in the example of FIG. 5A.

The second check valve 450 may be normally closed, creating a closed system of the solution source 114 and the dosing chamber 120. Expansion of the dosing chamber 120 reduces the pressure in the dosing chamber 120 under such conditions, creating a pressure gradient between the solution source 114 and the dosing chamber 120 that can move instillation solution from the solution source 114 through the first check valve 435 into the dosing chamber 120.

The amount of fluid transferred from the solution source 114 to the dosing chamber 120 can be calibrated by modifying certain system parameters. For example, the size of the dosing chamber 120 or the spring constant of the return spring 420 can be modified to change the stroke length of the diaphragm 410 in some embodiments. Alternatively or additionally, the size of the dosing chamber 120 may be increased or decreased according to therapeutic needs.

During a venting interval, negative pressure in the working chamber 560 can decrease until clamp 575 opens, as illustrated in the example of FIG. 5B. For example, if the first negative-pressure threshold exceeds the negative pressure in the working chamber 560, the force of the return spring 565 can overcome the pressure differential across the clamping piston 545, allowing the clamping piston 545 to return to a neutral position and opening the clamp 575.

If the second negative-pressure threshold exceeds the negative pressure in the working chamber 525, the force of the return spring 535 can exceed the pressure differential across the diaphragm 410, moving the diaphragm 410 and contracting the working volume of the dosing chamber 120, as also illustrated in the example of FIG. 5B.

The first check valve 435 may be normally closed, and contracting the dosing chamber 120 can increase the pressure in the dosing chamber under such conditions, creating a pressure gradient between the dosing chamber 120 and the fluid port 460 that can move instillation solution from the dosing chamber 120 through the second check valve 450 into the second fluid conductor 455. The first check valve 435 can prevent instillation solution from being returned to the solution source 114 as the pressure increases. In some embodiments, the instillation solution can be delivered to the dressing 102 through the fluid port 460. The bacterial filter 480 can prevent contamination of the instillation actuator 118.

The systems, apparatuses, and methods described herein may provide significant advantages. For example, some therapy systems are known to provide intermittent negative-pressure therapy modes, and the instillation pump 116 can leverage such modes to deliver therapeutic fluids without substantially modifying the therapy system. The instillation pump 116 can also reduce the disposable footprint of the therapy system 100 while providing cost-effective delivery of therapeutic fluids to tissue sites. Much of the mechanical system, such as the instillation actuator 118, can be used by more than one patient. For example, the instillation pump 116 can provide a continuous fluid pathway that can be separated from a mechanical actuator, allowing another fluid pathway to be installed. Tubing, valves, fluid chambers, and associated components can be removed in some embodiments. The combined assembly can also provide all pressure seals and fitments to allow disposable elements to be installed and to maintain actuation pressure within a pressure chamber. The instillation pump 116 can be readily attached to a dressing and solution source, which can be a significant feature for patients and care providers outside of a medical facility.

The disposable elements can be combined with the mechanical elements in a variety of different ways to provide therapy. For example, in some embodiments, the disposable and mechanical systems can be combined inline, externally mounted, or internally mounted.

While shown in a few illustrative embodiments, a person having ordinary skill in the art will recognize that the systems, apparatuses, and methods described herein are susceptible to various changes and modifications. For example, certain features, elements, or aspects described in the context of one example embodiment may be omitted, substituted, or combined with features, elements, and aspects of other example embodiments. Moreover, descriptions of various alternatives using terms such as "or" do not require mutual exclusivity unless clearly required by the context, and the indefinite articles "a" or "an" do not limit the subject to a single instance unless clearly required by the context. Components may be also be combined or eliminated in various configurations for purposes of sale, manufacture, assembly, or use. For example, in some configurations the dressing 102, the container 112, or both may be eliminated or separated from other components for manufacture or sale. In other example configurations, the controller 110 may also be manufactured, configured, assembled, or sold independently of other components.

The appended claims set forth novel and inventive aspects of the subject matter described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described herein may also be combined or replaced by alternative features serving the same, equivalent, or similar purpose without departing from the scope of the invention defined by the appended claims.

What is claimed is:

1. An apparatus for managing fluid in a system for negative-pressure therapy, the apparatus comprising:

a bellows having a fluid inlet and a fluid outlet;
a first check valve fluidly coupled to the fluid inlet;
a second check valve fluidly coupled to the fluid outlet;
a fluid conductor fluidly coupled to the second check valve;
a fluid port fluidly coupled to the fluid conductor and configured to be coupled to a negative-pressure source;
a fluid fitting fluidly coupled to the fluid conductor;
a filter fluidly coupled to the fluid conductor between the fluid port and the fluid fitting; and
an instillation actuator fluidly coupled to the fluid fitting, the instillation actuator configured to expand and contract the bellows, the instillation actuator comprising:
  a housing having a first-attachment arm rigidly coupled to a first end of the bellows, and a piston chamber fluidly coupled to the fluid fitting; and
  a piston having a second attachment arm operably engaged to the bellows and configured to be actuated by pressure changes in the piston chamber to expand and contract the bellows.

2. The apparatus of claim 1, wherein the fluid conductor comprises a constriction.

3. The apparatus of claim 1, wherein the filter comprises a bacterial filter.

4. The apparatus of claim 1, wherein the fluid port comprises a dressing pad.

5. The apparatus of claim 4, wherein the fluid conductor comprises a first conductor and a second conductor, and the dressing pad fluidly couples the first conductor to the second conductor.

6. The apparatus of claim 1, further comprising a liquid coupling fluidly coupled to the first check valve.

7. The apparatus of claim 1, further comprising a source of installation solution fluidly coupled to the first check valve.

8. The apparatus of claim 1, further comprising a negative-pressure source fluidly coupled to the fluid port.

9. The apparatus of claim 1, further comprising a negative-pressure source fluidly coupled to the fluid port, the negative-pressure source configured to draw instillation solution into the bellows through the fluid inlet during a negative-pressure interval and to expel instillation solution from the bellows through the fluid outlet during a venting interval.

10. A method for managing fluid in a system for negative-pressure and instillation therapy, the method comprising:
  fluidly coupling the apparatus of claim 1 to a dressing;
  applying the dressing to a tissue site;
  applying negative pressure to the tissue site for a first interval in which instillation solution is drawn into the bellows; and
  venting negative pressure from the tissue site for a second interval in which instillation solution is delivered from the bellows to the tissue site.

* * * * *